United States Patent [19]

Eckler

[11] 4,105,575

[45] Aug. 8, 1978

[54] PARTIAL RESOLUTION OF PENTAERYTHRITOL WASTE LIQUORS

[75] Inventor: Paul Eugene Eckler, Terre Haute, Ind.

[73] Assignee: IMC Chemical Group, Inc., Terre Haute, Ind.

[21] Appl. No.: 731,191

[22] Filed: Oct. 12, 1976

[51] Int. Cl.$^2$ ............................................. C07C 31/24
[52] U.S. Cl. ...................................... 252/182; 568/854
[58] Field of Search ..................... 252/182; 260/635 P

[56] References Cited

U.S. PATENT DOCUMENTS

| | | | |
|---|---|---|---|
| 2,369,083 | 2/1945 | Spurlin | 260/635 P |
| 2,372,555 | 3/1945 | Cox | 260/635 P |
| 2,372,602 | 3/1945 | Owens | 260/635 P |
| 2,407,920 | 9/1946 | Cox | 260/635 P |
| 2,978,514 | 4/1961 | Poynton | 260/635 P |
| 3,410,915 | 11/1968 | Greco et al. | 260/635 P |

FOREIGN PATENT DOCUMENTS 38,456  10/1958  Japan .................................. 260/635 P

*Primary Examiner*—Benjamin R. Padgett
*Assistant Examiner*—Irwin Gluck
*Attorney, Agent, or Firm*—Edward A. Figg; Howard E. Post

[57] ABSTRACT

A method is disclosed for partially resolving the components of a pentaerythritol waste liquor which contains pentaerythritol, polypentaerythritols, organic syrups, water, and an alkali metal formate which comprises acidifying the waste liquor to convert the alkali metal formate to formic acid and an alkali metal salt, adding a lower aliphatic alcohol to the acidified waste liquor to react with the formic acid to form a formate ester and to precipitate the alkali metal salt, removing the formate ester by distillation, and removing the precipitated alkali metal salt.

7 Claims, No Drawings

PARTIAL RESOLUTION OF PENTAERYTHRITOL WASTE LIQUORS

BACKGROUND OF THE INVENTION

Pentaerythritol is conventionally manufactured by the reaction of formaldehyde with acetaldehyde in the presence of an alkali metal hydroxide condensation catalyst, such as sodium hydroxide or potassium hydroxide. In addition to pentaerythritol; dipentaerythritol, tripentaerythritol, other polyhydroxy compounds (usually called organic syrups), and an alkali metal formate are also often produced. Through a rather complex series of concentrations and crystallizations, most of the products of the reaction are separated and recovered. Generally, however, a significant portion of the solid products cannot be further resolved by fractional crystallizations. The concentrated aqueous solution of such residual products is usually referred to herein as pentaerythritol waste liquor.

The conversion of the waste liquor to usable products is desirable because a substantial amount of pentaerythritol or pentaerythritol-like compounds are lost in the waste liquor, and also because the disposal of the waste liquor in an environmentally acceptable manner is costly.

The primary reason that the waste liquor from an alkali metal hydroxide catalyzed PE process is not a useful product is that it contains large quantities (i.e. from about 10% to 30% by wt.) of salts, principally alkali metal formate (usually referred to as ash). If the ash content is reduced to a low level, e.g. about 2% by wt., the mixture of polyhydroxy compounds of the waste liquor can be economically converted to a useful component of commercial resins, e.g. foundry core oils.

Various methods have been proposed for resolving the components of pentaerythritol waste liquors. The most common proposals have involved the extraction of the organic components out of a waste liquor or dried waste liquor with organic solvents such as aliphatic alcohols and tributylphosphate. Other methods proposed have been to remove the inorganic salt by passing the waste liquor through an ion exchange resin, and to remove the organic syrups with a bed of beads of a porous organic polymer.

SUMMARY OF THE INVENTION

An object of the present invention is to provide a method for partially resolving the components of a pentaerythritol waste liquor. Another object of the invention is to provide a method for reducing the ash content and formate content of a pentaerythritol waste liquor. Other objects and advantages of the invention will be apparent to those skilled in the art from the disclosure herein.

In accordance with the invention, there is disclosed a method for partially resolving the components of a pentaerythritol waste liquor which contains pentaerythritol, polypentaerythritols, organic syrups, water, and an alkali metal formate, comprising the steps of:
  acidifying the waste liquor with an acid selected from the group consisting of sulfuric acid, phosphoric acid, hydrochloric acid, and nitric acid at a concentration of from about 90% to about 125% of an amount equivalent to the alkali metal formate, thereby converting the alkali metal formate to formic acid and an alkali metal salt;
  adding to the acidified waste liquor a lower aliphatic alcohol of from 1 to about 3 carbon atoms in an amount sufficient to react with the formic acid to form a formate ester and to precipitate substantially all of the alkali metal salt; thereby forming an alcoholic waste liquor;
  removing the formate ester from the alcoholic waste liquor by distillation to form a formate-free waste liquor; and
  removing the precipitated alkali metal salt from the formate-free waste liquor.

DETAILED DESCRIPTION OF THE INVENTION

It has been found that upon acidification of a pentaerythritol waste liquor which is substantially saturated with an alkali metal formate, the formate is converted to formic acid and most of the resulting alkali metal salt precipitates. This phenomenon may be represented by the following equation:

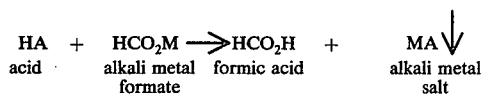

$$\text{HA} + \text{HCO}_2\text{M} \longrightarrow \text{HCO}_2\text{H} + \text{MA}\downarrow$$
acid   alkali metal   formic acid   alkali metal
         formate                         salt The reason that the alkali metal salt precipitates is believed to be because alkali metal formates are considerably more soluble in water than most other alkali metal salts. Accordingly, when the alkali metal in a saturated alkali metal formate solution is converted to another salt, that salt precipitates to the extent that it is insoluble in the waste liquor. It is apparent therefore that a significant reduction in ash content can be realized by acidifying the waste liquor.

Most inorganic acids function satisfactorily for the above-described purpose. Preferred acids include sulfuric acid, phosphoric acid, hydrochloric acid, and nitric acid. Sulfuric acid is most preferred because it provides two acidic protons, thus requiring lower concentrations than other acids, and also because it usually is less costly and is less corrosive than other inorganic acids. Although phosphoric acid is polyhydric, only the first dissociation constant is higher than that of formic acid, therefore, phosphoric acid acts as a monohydric acid in the above reaction. There is a potential hazard in the use of nitric acid, because explosive nitrate esters of polyhydroxy compounds may be formed.

Since it is desirable to convert as much of the alkali metal formate to an alkali metal salt as possible, the concentration of the acid should be at least substantially equivalent to the alkali metal formate, e.g. at least about 90% of an amount equivalent to the alkali metal formate. By an equivalent amount is meant that amount of a monohydric acid which is equimolar to the alkali metal formate, and that amount of a dihydric acid which is in a 1:2 mole ratio of acid to alkali metal formate. An excess of acid may advantageously be used; however, in the case of sulfuric acid, as the concentration of the acid exceeds the equivalency point, an increasing amount of bisulfate, as opposed to sulfate, is produced. Since alkali metal bisulfates are more soluble than alkali metal sulfates, increasing the acid concentration substantially above the equivalency point has a deleterious effect on the ash content of the waste liquor. Furthermore, large excesses of acid increase processing costs, inasmuch as they must ultimately be removed from the product. In balancing the desire to convert as much as of the alkali metal formate to an alkali metal salt as possible against the desire to minimize the formation of an alkali metal bisulfate, it has been found that a preferred range of sulfuric acid concentration is from about 90% to about 125% of an amount equivalent to the alkali metal formate. The most preferred range of acid concentration is from about 100% to about 110% of an amount equivalent to the alkali metal formate.

Although a substantial amount of the alkali metal (e.g. about 60%) in the waste liquor can be precipitated by acidification, a further reduction to about 10% of the initial amount or less is desirable. Removal of the formic acid is also very desirable. It has been discovered that both of these goals can be accomplished by adding to the acidified waste liquor a lower organic alcohol of from 1 to about 3 carbon atoms, e.g. methanol, ethanol, propanol, alkyl alcohol, propargyl alcohol, etc. Since the alkali metal salt is substantially insoluble in a lower organic alcohol, the majority of the remaining alkali metal is thus precipitated. It should be noted that neither the alkali metal formate or bisulfate is precipitated by the addition of alcohol, therefore, the combination of the acidification step and the alcohol addition are required for substantially quantitative ash precipitation.

In addition to precipitating the remaining alkali metal salt, the alcohol reacts with the formic acid to form a formate ester. The formate ester may advantageously be removed from the alcoholic waste liquor by distillation. The formate ester is preferably removed by distillation as it is formed, since removal of ester provides an equilibrium condition favorable to substantially complete formate removal.

The precipitated alkali metal salt is conveniently removed from the waste liquor after distillation of the formate ester. Removal of the alkali metal salt may be by any convenient method, such as filtration or centrifugation. The excess alcohol may also be removed from the waste liquor by distillation, preferably after the alkali metal salt has been removed.

The particular organic alcohol chosen for the method is not critical, but is preferably methanol. The amount of alcohol used in generally enough to react with all of the formic acid and to precipitate substantially all of the alkali metal salt. At least about 3 moles of alcohol per mole of formic acid is generally satisfactory. The alcohol is preferably employed at about 5 moles or more per mole of formic acid. (Note: The amount of alkali metal formate originally in the waste liquor is determined gravimetrically as the sulfated ash.

After removing substantially all of the ash and the formate ester by the method of this invention the residual amounts of acid and alkali metal in the waste liquor may be removed, for instance by ion exchange.

It is thus apparent that a method for partially resolving the components of a pentaerythritol waste liquor which satisfies the objects recited above has been discovered. After being treated by the method of this invention, the waste liquor is of sufficient quality for use in certain alkyd resins. Furthermore, the formate ester is a useful product in itself as a fumigant, solvent, or chemical intermediate, or it may be hydrolyzed with sodium hydroxide back to the alcohol, which may be recycled, and sodium formate which is marketable product.

The invention is further illustrated by the following examples which are not intended to be limiting.

EXAMPLE I

A 1 kg. sample of pentaerythritol waste liquor, resulting from a process utilizing a sodium hydroxide condensation catalyst, was charged into a 2-liter, 3-neck round bottomed flask, which was equipped for distillation. Sulfuric acid (96%) (215 g, 2.1 mole) was added, dropwise, with stirring, over a period of about 30 minutes. Solids precipitated immediately. Methanol (712 g, 22.2 mole) was then added by dropping funnel. The methyl formate, which began refluxing immediately, was distilled from the reaction mixture. The bulk of the distillate (250 g) was collected at 32° C The pot bottoms were cooled to about 25° C and filtered to remove 274.5 g of precipitated sodium sulfate. The excess methanol was then recovered from the filtrate as a second fraction distilling up to 80° C. The residual waste liquor contained 2.0 wt.% $Na_2SO_4$, determined gravimetrically as the sulfated ash.

EXAMPLE II

The experiment of Example I was repeated in all essential details except 317 g (9.9 mole) of methanol was used. The residual waste liquor contained 5.25 wt.% $Na_2SO_4$, determined gravimetrically as the sulfated ash.

EXAMPLE III

The experiment of Example I was repeated in all essential details except 220 g (2.15 mole) of 96% sulfuric acid and 218 g (6.8 mole) of methanol were used. The residual waste liquor contained 13.39 wt.% $Na_2SO_4$, determined gravimetrically as the sulfated ash.

EXAMPLE IV

The experiment of Example I was repeated in all essential details except 205 g (2.0 mole) of 96% sulfuric acid and 218 g (6.8 mole) of methanol were used. The residual waste liquor contained 10.98 wt.% $Na_2SO_4$, determined gravimetrically as the sulfated ash.

EXAMPLE V

The experiment of Example I is repeated in all essential details except 484 g (4.2 mole) of 85% phosphoric acid was substituted for sulfuric acid and 920 g (20 mole) of ethanol was substituted for methanol. Monosodium phosphate and ethyl formate should be recovered from the waste liquor and the residual waste liquor should be low in ash.

EXAMPLE VI

The experiment of Example I is repeated in all essential details except 425 g (4.2 mole) of 36% hydrochloric acid is substituted for sulfuric acid and 1202 g (20 mole) of n-propanol is substituted for methanol. Sodium chloride and propyl formate should be recovered from the waste liquor, and the residual waste liquor should be low in ash.

EXAMPLE VII

The experiment of Example I is repeated in all essential details except 384 g (4.2 mole) of 69% nitric acid is substituted for sulfuric acid and 1202 g (20 mole) of 2-propanol is substituted for methanol. Sodium nitrate and 2-propyl formate should be recovered from the waste liquor, and the residual waste liquor should be low in ash.

EXAMPLE VIII

The experiment of Example I is repeated in all essential details except a pentaerythritol waste liquor resulting from a process utilizing a potassium hydroxide condensation catalyst is used. Potassium sulfate and methyl formate should be recovered from the waste liquor, and the residual waste liquor should be low in ash.

I claim:

1. A method for partially resolving the components of a pentaerythritol waste liquor which contains pentaerythritol, polypentaerythritols, organic syrups, water and is substantially saturated with an alkali metal formate, comprising the steps of:

acidifying the waste liquor with an acid selected from the group consisting of sulfuric acid, phosphoric acid, hydrochloric acid, and nitric acid at a concentration of from about 90% to about 125% of an amount equivalent to the alkali metal formate, thereby converting the alkali metal formate to formic acid and a partially precipitated alkali metal salt;

adding to the acidified waste liquor a lower organic alcohol of from 1 to about 3 carbon atoms in an amount sufficient to react with the formic acid to form a formate ester and to precipitate substantially all of the alkali metal salt which was not precipitated in the acidification step; thereby forming an alcoholic waste liquor;

removing the formate ester from the alcoholic waste liquor by distillation to form a formate-free waste liquor; and removing the precipitated alkali metal salt from the formate-free waste liquor.

2. The method of claim 1 wherein the alkali metal formate is sodium formate, the waste liquor is acidified with sulfuric acid, and the lower organic alcohol is methanol.

3. The method of claim 2 wherein the sulfuric acid is employed at a concentration of from about 100% to about 110% of an amount equivalent to the sodium formate and the methanol is employed in at least about a 3:1 mole ratio of alcohol to sodium formate.

4. The method of claim 1 wherein the alkali metal formate is sodium formate, the waste liquor is acidified with sulfuric acid, and the lower organic alcohol is ethanol.

5. The method of claim 1 wherein the waste liquor is acidified with phosphoric acid; and the lower organic alcohol is ethanol.

6. The method of claim 1 wherein the waste liquor is acidified with hydrochloric acid; and the lower organic alcohol is n-propanol.

7. The method of claim 1 wherein the waste liquor is acidified with nitric acid and the lower organic alcohol is 2-propanol.

* * * * *

UNITED STATES PATENT AND TRADEMARK OFFICE
CERTIFICATE OF CORRECTION

PATENT NO. : 4,105,575

DATED : August 8, 1978

INVENTOR(S) : Paul E. Eckler

It is certified that error appears in the above—identified patent and that said Letters Patent are hereby corrected as shown below:

Column 3, line 44, "in" should read -- is --

Signed and Sealed this

Nineteenth Day of June 1979

[SEAL]

Attest:

RUTH C. MASON
Attesting Officer

DONALD W. BANNER
Commissioner of Patents and Trademarks